United States Patent [19]

Esser

[11] Patent Number: 5,932,199
[45] Date of Patent: Aug. 3, 1999

[54] ANTIPERSPIRANT OR DEODORANT COMPOSITION

[75] Inventor: Isabelle Claire Helene Marie Esser, Wirral, United Kingdom

[73] Assignee: Helen Curtis, Inc., Chicago, Ill.

[21] Appl. No.: 08/991,455

[22] Filed: Dec. 16, 1997

[30] Foreign Application Priority Data

Dec. 23, 1996 [GB] United Kingdom .................. 9626793

[51] Int. Cl.⁶ ................................ A61K 7/32; A61K 7/00
[52] U.S. Cl. ............................. 424/65; 424/400; 424/401
[58] Field of Search ............................ 424/65, 400, 401

[56] References Cited

U.S. PATENT DOCUMENTS

| | | | |
|---|---|---|---|
| 4,126,679 | 11/1978 | Davy et al. | 424/66 |
| 4,137,306 | 1/1979 | Rubino | 424/68 |
| 4,781,917 | 11/1988 | Luebbe et al. | 424/65 |
| 5,540,853 | 7/1996 | Trinh et al. | 510/101 |

FOREIGN PATENT DOCUMENTS

| | | |
|---|---|---|
| 117070 | 8/1984 | European Pat. Off. . |
| 2430897 | 1/1976 | Germany . |
| 96/35408 | 11/1996 | WIPO . |

OTHER PUBLICATIONS

International Search Report Application No. PCT/EP 97/06959 dated May 12, 1998.

*Primary Examiner*—Shelley A. Dodson
*Attorney, Agent, or Firm*—Matthew Boxer

[57] ABSTRACT

A substantially anhydrous stick antiperspirant composition comprising from 1–35% of an antiperspirant active, a carrier for the active and from 0.1 to 30% of a moisturising cream comprising one or more humectants, which comprise at least one hydroxyl group and a perfume carrier material.

12 Claims, No Drawings

ANTIPERSPIRANT OR DEODORANT COMPOSITION

The invention relates to antiperspirant or deodorant compositions, but in particular antiperspirant compositions, comprising a moisturising cream suitable for topical application to human skin, especially solid compositions suitable for use as a cosmetic stick together with a stick holder.

The deodorant and antiperspirant market is dominated with products based on aluminium or zirconium salts which are intended to prevent, or at least control, perspiration at the skin surface, particularly on the underarm, whilst often simultaneously providing a perceived degree of deodorancy.

Various physical forms of antiperspirant compositions are known, for example aerosol, lotion, or solid form.

When the antiperspirant is provided as a solid composition for use in "stick" form, it is known to incorporate the active components which may be present in the composition, such as for example the aluminium or zirconium salt and the other components of the composition, in a cosmetically acceptable vehicle comprising largely silicone oils (whether volatile or non-volatile), and a matrix of long chain fatty acids which act as a structurant.

For example, in U.S. Pat. No. 4,126,679 (Armour-Dial), there is described the possibility of making solid stick antiperspirant compositions comprising powdered astringent metallic salts, suspended in a matrix comprising volatile silicone oils, and 15 to 70% alcohols selected from long-chain water insoluble aliphatic alcohols having 16–22 carbon atoms in the chain.

EP-B-117,070 (Procter & Gamble) describes a solid stick antiperspirant composition, which comprises 5 to 20% of a long chain fatty alcohol having 8 to 18 carbon atoms in its chain, 35 to 55% of a volatile polydimethyl silicone, 10 to 70% of an astringent antiperspirant salt, and 1 to 3% by weight of the total long chain fatty alcohol level of the composition of an additional long chain fatty alcohol selected from $C_{20}$–$C_{26}$ fatty alcohols, or mixtures thereof.

A problem with existing solid stick formulations in general is poor sensory properties as perceived by the user, and their perceived skin unfriendliness. More particularly, the presence of volatile carriers such as volatile silicone and indeed deodorant and antiperspirant actives is perceived to have a drying and tightening effect on a user's skin following application resulting in dry skin, reduced skin elasticity and an unpleasant skin sensation.

According to a first aspect of the invention there is provided a substantially anhydrous stick antiperspirant or deodorant composition comprising an antiperspirant or deodorant active, a carrier for the active and a moisturising cream comprising one or more humectants which comprise at least one hydroxyl group, and a perfume carrier material.

An object of the invention is to provide such a composition which has excellent antiperspirant efficacy, excellent cosmetics and aesthetics such as comfort in use and smoothness on application.

According to a further and preferred aspect of the invention there is provided a substantially anhydrous antiperspirant stick composition suitable for topical application to human skin, comprising:

i. an effective amount of an antiperspirant active;
ii. a volatile silicone;
iii. a structurant;
iv. a moisturising cream containing a humectant which has at least one hydroxyl group; and
v. a perfume carrier material.

Suitably, the antiperspirant or deodorant active comprises 1–35% by weight of the composition.

Advantageously, the composition additionally comprises a non-volatile emollient.

In a particularly preferred embodiment, the invention provides a substantially anhydrous stick antiperspirant composition suitable for topical application to the human skin, comprising:

i. 10–25% by weight of the total composition of an antiperspirant active;
ii. 5–60% by weight of the total composition of a linear or cyclic volatile silicone;
iii. 5 to 30% by weight of the total composition of long chain water insoluble aliphatic alcohols having 16–22 carbon atoms in the chain;
iv. 0.1 to 30% by weight of a moisturising cream, one of whose components is a humectant having at least one hydroxy group; and
v. 0.1–5% of a perfume carrier material.

We have surprisingly found that a moisturising cream containing a humectant having at least one hydroxyl group can be incorporated into an antiperspirant or deodorant stick composition to produce a stick composition which has improved and attractive cosmetic characteristics expected of such sticks, as well as satisfactory efficacy.

Humectants are well know in the art and are cosmetic ingredients intended to increase the water content of the top layers of the skin. This group of ingredients includes primarily hygroscopic agents employed for this specific purpose. Humectants of particular interest for the present invention are polyols and alcohols such as sorbitol, glycerol, ethylene glycol, propylene glycol or mixtures thereof.

The composition according to the invention comprises a hygroscopic material known as a humectant, preferably a polyol or an alcohol at 0.1% to 15%, preferably 0.5 to 8%, most preferably 0.5 to 3% by weight of the total composition.

Surprisingly, we also found that to obtain a composition of superior aesthetics according to the invention incorporating a moisturising cream, which includes one or more humectant, in particular polyols, a further ingredient needed to be incorporated in the composition. We found that materials which can interact either physically or chemically with the humectant present in the moisturising cream to bind it are effective. Materials which act as perfume carriers have been found to be particularly effective.

The incorporation of such a perfume carrier material has been found to be essential in compositions according to the invention in that it prevents the stick composition from becoming gritty during or shortly after manufacture, and as such losing the superior aesthetic properties such as smoothness on application and comfort on use which are obtained by the inclusion of the moisturising cream. Without wishing to be bound by theory, it is suspected that the presence of the perfume carrier material in the composition prevents the antiperspirant active from crystallising or agglomerating, which would otherwise be caused by an interaction between the humectant and the antiperspirant active, thereby preventing the composition from developing a gritty texture, which is perceived by and unacceptable to the user.

One parameter that has to be very closely controlled with stick formulations is the hardness of the stick. This is important not only because it determines the storage properties of the stick, in particular the resistance of the stick to degradation caused by temperature extremes, but also because it determines the deposition of antiperspirant composition that occurs when the stick is used for a given application stroke.

Viewed against the prior art, it has been found that cosmetic sticks with desirable hardness, pay off and skin feel can be made incorporating a moisturising cream.

Preferably, the moisturising cream in the stick composition according to the invention will normally be a dispersion, and the term can equally be applied to non-aqueous products such as wax-solvent based products and ointments. The term also includes dispersion products of cream consistency.

Moisturising creams used in the compositions according to the invention are those which aid retention of water to plasticise outer layers of the epidermis to promote soft, smooth skin. If water is lost more rapidly from the stratum corneum that it is received from the lower layers of the epidermis, the skin becomes dehydrated and loses its flexibility.

Moisturising creams according to the invention will typically work by the well-known route of humectancy either alone or in combination with the other two main routes of moisturisation, namely occlusion and restoration of deficient materials.

Typically the moisturising cream is present in the composition at a level of 0.1 to 30%, more preferably 10 to 28% by weight.

The approach consists in the use of humectants to attract water from the surrounding environment, thereby supplementing the skin's water content. Occlusion consists of reducing the rate of transepidermal water loss through old or damaged skin or in protecting otherwise healthy skin from the effect of a drying environment. The last approach is to determine the mechanism of the skin moisturisation process, and supplement the skin in its deficiencies.

In compositions according to the invention, it is the moisturising cream component of the composition which provides a moisturising benefit.

The composition according to the invention will be substantially anhydrous and will therefore comprise water at a level less than 2%, preferably less than 1% and most preferably less than 0.2% by weight of the total composition.

The perfume carrier in compositions according to the invention comprises a material which can strongly bind to the humectant. This is taken to mean form of chemical or physical binding, and can include effects such as adsorption, absorption, H-bonding, and so on. Particularly effective are materials known as perfume carriers, such as fumed silica, calcite, zeolite MAP, or finely ground zeolite 4A, at least a level of 0.1% and up to a level up 15%, preferably up to 8%, most preferably up to 5% by weight of the total composition. Suitable silicas include commercial grade Aerosil 200 or Cab-o-Sil. Other suitable perfume carrying materials for use in compositions according to the invention are described in PTC/GB95/05000, published Jul. 18, 1996, the contents of which are incorporated herein by reference.

The composition according to the invention may also comprise an antiperspirant or deodorant active. Examples of suitable antiperspirant actives include aluminium salts, zirconium salts, aluminium and/or zirconium complexes, for example aluminium halides, aluminium hydroxy halides, zirconyl oxyhalides, zirconyl hydroxyhalides, and mixtures thereof. Useful zirconium salts include zirconium hydroxychloride and zirconium oxychloride. Other generally used actives will be known to those skilled in the art. Preferred actives include AAZG (Activated Aluminium Zirconium Glycine), ZAG (Zirconium Aluminium Glycine), and AACH (Activated Aluminium Chorohydrate).

The amount of antiperspirant or deodorant active present in the composition according to the invention is from 1.0 to 35%, preferably 5 to 30%, most preferably 10 to 25% by weight of the total composition.

The composition according to the invention may also comprise as part of the carrier one or more long chain fatty alcohols as structurants. Such materials are well known in the art and include fatty acids, fatty alcohols, fatty acid esters, and fatty acid amides, having fatty chains of from 8 to 30 carbons atoms. Typically, the structurant can comprise 5 to 40%, preferably 5 to 30% by weight of the total composition of long chain water insoluble aliphatic alcohols having 12–22 carbon atoms in the chain, more preferably having 16–22 carbon atoms in the chain. Stearyl alcohol is particularly preferred.

The composition according to the invention may also comprise a linear or cyclic volatile silicone. Useful silicones include cyclic or linear polydimethyl silicones containing from 3 to 9, preferably 4 to 6, silicon atoms.

Examples of suitable volatile silicones include polydimethyl cyclosiloxanes, having a viscosity of less than 10 $mm^2s^{-1}$, examples of which are DOW CORNING fluids 344 and 244 (tetramer) and DOW CORNING Fluids 245 and 345 (pentamer). Other suitable silicones include hexamethyldisiloxane having a viscosity of not more than 0.65 $mm^2s^{-1}$, for example DOW CORNING 200 Fluid, which has a viscosity of 0.65 $mm^2s^{-1}$ as determined in accordance with the method provided in the data sheets provided by the manufacturer on these compounds.

The preferred volatile silicones are the cyclic forms.

The amount of volatile silicone present in the composition according to the invention may typically be from 1 to 60%, preferably from 5 to 60%, most preferably 20 to 55% by weight of the total composition.

The composition according to the invention can optionally comprise other ingredients, in addition to those already identified, depending on the nature and form of the finished product.

Examples of other ingredients which can optionally be present in the composition according to the invention include:

Emollients, such as non-volatile silicones, hydrocarbons or mineral oils. Suitable non-volatile silicones include polydimethylsiloxane having a viscosity in excess of $5mm^2s^{-1}$, for example, from 50 to 1000 $mm^2s^{-1}$, such as DOW CORNING 200 Fluids (standard viscosities 50–1000 $mm^2s^{-1}$). Other useful emollients include PEG 400 distearate, and ethylene oxide and/or propylene oxide condensation products having the following formula:

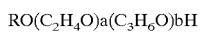

$$RO(C_2H_4O)a(C_3H_6O)bH$$

where R is either hydrogen or a hydrocarbon chain having from about 2 to 20 carbon atoms, and a and b are each from about 0 to 35 and a+b is from about 5 to 35.

Examples of such a emollients are Fluid AP (Amerchol) and Ethylflo (Union Carbide).

Still further emollients suitable for use in the present solid stick compositions include fatty acid and fatty alcohol esters and water insoluble ethers.

Fillers can comprise up to about 10% of the total product and are normally less costly that the essential components of the invention thereby reducing overall cost. Suitable fillers include aluminium stearate, aluminium tri-stearate, calcium stearate, talc or finely divided polyethylene, an example of which is ACUMIST B18.

Fragrances typically comprise up to about 1% of the total product.

Other optional ingredients are other cosmetic adjuncts conventionally employed in stick deodorant products.

A preferred optional component includes a natural or synthetic wax such as castor wax, Synchrowax HRC, Carnaubau, beeswax, silicone waxes and glycerol monostearate and mixture thereof at levels of from about 1 to 10% preferably 2 to 8%. If present, the wax is believed to enhance structural stability of the composition in the molten state.

The ingredients which can optionally be present in the composition can conveniently form the balance of the composition.

The composition according to the invention can take the form of a solid product suited to or adapted for topical application to human skin. One convenient form of the composition according to the invention is a solid stick, usually contained in a suitable holder or dispenser to enable it to be applied to the area of the skin, particularly the underarm, where control of perspiration and deodorancy is required.

The invention also provides for the use of a solid stick antiperspirant composition, in accordance with the invention, as herein defined, in perspiration control, following topical application to human skin.

The antiperspirant sticks of this invention can be manufactured using methods known in the art. Typically the method consists of melting the waxes in the carrier liquid in a vessel at a temperature of 65–95° C. with stirring. Other non-particulate ingredients (e.g. emollient and preservatives) are added slowly with mixing, and subsequently all particulate ingredients such as the antiperspirant active, talc and so on are added slowly with stirring, at around 65° C. Finally, perfume is added to the composition with stirring. The molten composition may then be cast into sticks of the desired shape and cooled.

Care should be taken in the processes of making these compositions to maintain uniform distribution of the particulate materials throughout the antiperspirant stick.

It has been found highly advantageous for processing the stick according to the invention to premix in a liquid carrier the humectant with the perfume carrier or any material performing the same function, and homogenise this mixture thoroughly using an homogeniser device at high shear with a rotor stator system, which ensures that all materials pass through a high shear zone, i.e the gap between the rotor stator set, to allow the binding of these components to occur. The minimum shear threshold (i.e. "high shear") is 1500 to 2000 sec$^{-1}$. Suitable high shear devices include devices such as a Moritz high shear turbo mixer, or a Silverson. The composition can then have added the structurant components of the composition, be heated until the components are molten, and the antiperspirant active added along with other particulates in the composition; the composition is then cooled, perfume added, and casted into barrels.

EXAMPLES

The invention is further illustrated by the following examples.

Example 1

The following cream was formulated according to the following protocol. All ingredients were heated to 75° C. The cream texture was obtained by using a high shear homogeniser as the formulated product is cooling, providing a flowable product.

| component | weight % |
|---|---|
| stearyl alcohol | 17.2 |
| hydrogenated castor oil | 2.4 |
| PEG-8 Distearate | 2.4 |
| PPG-14 butyl ether | 40.0 |
| Volatile silicone | 30.0 |
| glycerol | 8.0 |
| Total | 100.0 |

The above cream was shown to be moisturising in-vivo as it increased the skin elasticity as measured by DIASTRON Dermal Torque Meter, and the skin hydration as measured using a Corneometer CM 820 PC Skin Hygrometer after one day compared to no treatment on a five day test protocol. The increase in skin elasticity and skin hydration versus untreated area were significant at 95% confidence level after one day.

Example 2

An antiperspirant composition containing 25% of the moisturising cream of example 1 and suitable for a stick applicator was formulated without a perfume carrier.

A typical method of manufacture was used, i.e. the waxes were molten in the liquids, the particulate ingredients were added slowly with stirring, and the molten composition was then cast into sticks.

The resulting stick was found to be gritty giving unacceptable in-use properties and uncomfortable application as well as reduced efficacy.

Example 3

Two identical antiperspirant compositions containing 25% of the moisturising cream of example 1 and suitable for a stick applicator were formulated adding silica (Aerosil 200 fumed silica) at a level of 2% by weight of the total composition.

The first stick was manufactured using the same method as in example 2.

The resulting stick was found to be gritty giving unacceptable in-use properties, including uncomfortable application (abrasion of the skin) which was noticed by the users.

The second stick was manufactured according the process of the present invention; i.e. the humectant, the perfume carrier and the solvent carrier were premixed at high shear using a homogeniser device with a rotor stator system, ensuring that the mixture pass through a high shear zone. The minimum shear threshold was 1500 sec$^{-1}$. Then the waxes were molten in the mixture and the particulate ingredient added, slowly with stirring, and the molten composition was then cast into sticks.

The resulting stick was found to have good texture (smooth), good cosmetic and aesthetic properties such as comfort in use, smoothness on application and non-sting on application, and gave good wetness and odour control.

Example 4

An antiperspirant compositions containing 25% of the moisturising cream of example 1 and suitable for a stick applicator was formulated adding 2.5% calcite by weight of the total composition.

The stick composition was manufactured according to the manufacturing process disclosed in the invention and specified in example 3.

The resulting stick was found to have good texture (smooth), good cosmetic and aesthetic properties such as comfort in use, smoothness on application and non-sting on application, and give good wetness and odour control.

Example 5

An identical stick composition as described in example 2 was manufactured according to the manufacturing process disclosed in the invention and specified in example 3.

The resulting stick was found to be gritty giving unacceptable in-use properties, uncomfortable application (abrasion of the skin) noticed by the users.

I claim:

1. A substantially anhydrous stick antiperspirant composition comprising from 1–35% of an antiperspirant active, a carrier for the active and from 0.1 to 30% of a moisturising cream comprising one or more humectants, which comprise at least one hydroxyl group and a perfume carrier material.

2. An antiperspirant composition according to claim 1 wherein the composition additionally comprises a non-volatile emollient.

3. An antiperspirant composition according to claim 1 wherein the moisturising cream comprises a humectant selected from the group consisting of sorbitol, glycerol, propylene glycol, ethylene glycol and mixtures thereof.

4. An antiperspirant composition according to claim 1 wherein the humectant is present at a level of 0.1 to 15% by weight of the total composition.

5. An antiperspirant composition according to claim 1 additionally comprising a structurant.

6. An antiperspirant composition according to claim 5 wherein the structurant comprises 5 to 40% by weight of the composition of $C_{18}$–$C_{22}$ long chain fatty alcohols.

7. An antiperspirant composition according to claim 1 wherein the carrier comprises 1 to 60% by weight of the composition of a volatile silicone.

8. An antiperspirant composition according to claim 1 additionally comprising from 1 to 10% of a natural or synthetic wax.

9. A substantially anhydrous antiperspirant stick composition suitable for topical application to human skin, comprising:

i. an effective amount of an antiperspirant active;

ii. a volatile silicone;

iii. a structurant iv. a moisturising cream containing a humectant; and v. a perfume carrier material.

10. A process for manufacturing a substantially anhydrous antiperspirant stick comprising an antiperspirant active, a liquid carrier, a structurant and a humectant, comprising:

blending together under high shear the liquid carrier, the humectant and the perfume carrier;

adding the structurant to the blend;

heating the composition until the structurant has melted;

adding the antiperspirant active and all other non-fragrance components of the composition;

cooling the composition and adding any fragrance; and casting the composition.

11. A process for manufacturing a substantially anhydrous antiperspirant stick comprising an antiperspirant active, a liquid carrier, a structurant and a humectant, comprising:

heating and blending together under high shear the liquid carrier, the humectant, the perfume carrier, and the structurant;

adding the antiperspirant active and all other non-fragrance components of the composition;

cooling the composition and adding any fragrance; and casting the composition.

12. An antiperspirant composition according to claim 5, wherein said structurant is selected form the group consisting of fatty acids, fatty alcohols, fatty acid esters, and fatty acid amides, wherein fatty chains of from 8 to 30 carbon atoms are present.

* * * * *